(12) United States Patent
Scheib et al.

(10) Patent No.: US 9,990,731 B2
(45) Date of Patent: Jun. 5, 2018

(54) SYSTEMS AND METHODS FOR EVALUATING MOTION TRACKING FOR RADIATION THERAPY

(71) Applicant: Varian Medical Systems International AG, Cham (CH)

(72) Inventors: Stefan G. Scheib, Wadenswil (CH); Christof Baltes, Oberwil-Lieli (CH); Kristijan Macek, Maribor (SI)

(73) Assignee: Varian Medical Systems International AG, Cham (CH)

( * ) Notice: Subject to any disclaimer, the term of this patent is extended or adjusted under 35 U.S.C. 154(b) by 203 days.

(21) Appl. No.: 14/994,766

(22) Filed: Jan. 13, 2016

(65) Prior Publication Data

US 2017/0200276 A1 Jul. 13, 2017

(51) Int. Cl.
*G06T 7/00* (2017.01)
*G06T 7/20* (2017.01)
*G06K 9/62* (2006.01)
*A61N 5/10* (2006.01)

(52) U.S. Cl.
CPC .............. *G06T 7/20* (2013.01); *A61N 5/1047* (2013.01); *A61N 5/1049* (2013.01); *A61N 5/1071* (2013.01); *A61N 5/1075* (2013.01); *G06K 9/6267* (2013.01); *G06T 7/0012* (2013.01); *A61N 2005/1054* (2013.01); *A61N 2005/1072* (2013.01); *A61N 2005/1076* (2013.01)

(58) Field of Classification Search
CPC .. A61N 5/1045; A61N 5/1047; A61N 5/1071; G06K 9/6267; G06T 7/0012; G06T 7/20
See application file for complete search history.

(56) References Cited

U.S. PATENT DOCUMENTS

2009/0283682 A1* 11/2009 Star-Lack .............. A61B 6/032
250/363.1

OTHER PUBLICATIONS

Renner et al., "A dose delivery verification method for conventional and intensity-modulated radiation therapy using measured field fluence distributions", Medical Physics, vol. 30, No. 11, Nov. 2003, 11 pages.
Van Elmpt et al., "3D in Vivo Dosimetry Using Megavoltage Cone-beam CT and EPID dosimetry", Int. J. Radiation Oncology Biol. Phys., vol. 73, No. 5, pp. 1580-1587, 2009, 8 pages.
Podestal et al., "Time dependent pre-treatment EPID dosimetry for standard and FFF VMAT", Phys. Med. Biol. 59, 4749-4768, Aug. 4, 2014, 21 pages.

(Continued)

*Primary Examiner* — Stephen R Koziol
*Assistant Examiner* — Shaghayegh Azima
(74) *Attorney, Agent, or Firm* — Vista IP Law Group, LLP

(57) ABSTRACT

An apparatus includes: a processor configured for obtaining a first image that corresponds with a first multi-leaf collimator (MLC) configuration, wherein the first image is generated when the MLC is stationary, obtaining a second image that corresponds with a second MLC configuration, wherein the second image is generated when the MLC and/or another component of a radiation machine is being operated to track a motion, and performing an analysis based at least in part on the first image and the second image to obtain a result; and a non-transitory medium for storing the result.

20 Claims, 4 Drawing Sheets

(56) References Cited

OTHER PUBLICATIONS

King et al., "Development and testing of an improved dosimetry system using a backscatter shielded electronic portal imaging device", Med. Phys. 39(5), May 2012, 9 pages.
Nijsten et al., "A global calibration model for α-Si EPIDs used for transit dosimetry", Med. Phys. 34(10), Oct. 2007, 13 pages.
"Athena for Machine QA", EPIdos, Mar. 21, 2013, 2 pages.
Nicolini et al., "GLAaS: An absolute dose calibration algorithm for an amorphous silicon portal imager. Applications to IMRT verifications", Med. Phys. 33(8), Aug. 2006, 13 pages.
"Hera for IMRT QA", EPIdos, Jun. 27, 2011, 2 pages.

\* cited by examiner

SYSTEMS AND METHODS FOR EVALUATING MOTION TRACKING FOR RADIATION THERAPY

FIELD

The field of the application relates to systems and methods for radiation therapy, and more specifically, to systems and methods for evaluating motion tracking for radiation therapy.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. During a radiation therapy, a radiation source may be rotated around a patient to deliver radiation from different angles at target region inside the patient. The radiation source may be mounted on an arm or a ring gantry. In certain radiation therapy, the patient support supporting the patient may also be moved.

Before treatment radiation is delivered by a radiation treatment machine, a machine quality assurance (QA) procedure may be performed to ensure that the treatment machine meets certain criteria for performing the treatment procedure. Also, pre-treatment QA procedure may be performed to ensure that a treatment plan (when being executed by the treatment machine) will meet certain criteria for delivering treatment radiation to the patient.

Applicant of the subject disclosure determines that it may be desirable to provide a new system and method for performing these QAs and/or other QA(s).

SUMMARY

A method includes: obtaining a first image that corresponds with a first multi-leaf collimator (MLC) configuration, wherein the first image is generated when the MLC is stationary; obtaining a second image that corresponds with a second MLC configuration, wherein the second image is generated when the MLC and/or another component of a radiation machine is being operated to track a motion; performing an analysis based at least in part on the first image and the second image using a processor to obtain a result; and storing the result in a non-transitory medium.

Optionally, the first image is a part of a first set of images that are obtained while the MLC is in different respective static configurations.

Optionally, the method further includes selecting the first image from the first set of images that corresponds with the second image.

Optionally, the method further includes selecting the first image from the first set of images, selecting a third image from the first set of images, and performing an interpolation based on the first and third images to determine an interpolated parameter that corresponds with the second image.

Optionally, the analysis is performed to verify a treatment plan before a treatment is performed.

Optionally, the analysis is performed to verify treatment.

Optionally, the analysis is performed in real time during treatment.

Optionally, the motion comprises a real or artificial motion.

Optionally, the analysis comprises a time-resolved analysis.

An apparatus includes: a processor configured for obtaining a first image that corresponds with a first multi-leaf collimator (MLC) configuration, wherein the first image is generated when the MLC is stationary, obtaining a second image that corresponds with a second MLC configuration, wherein the second image is generated when the MLC and/or another component of a radiation machine is being operated to track a motion, and performing an analysis based at least in part on the first image and the second image to obtain a result; and a non-transitory medium for storing the result.

Optionally, the first image is a part of a first set of images that are obtained while the MLC is in different respective static configurations.

Optionally, the processor is further configured for selecting the first image from the first set of images that corresponds with the second image.

Optionally, the processor is configured for selecting the first image from the first set of images, selecting a third image from the first set of images, and performing an interpolation based on the first and third images to determine an interpolated parameter that corresponds with the second image.

Optionally, the processor is further configured to verify a treatment plan before a treatment is performed based on the result.

Optionally, the processor is further configured to verify treatment based on the result.

Optionally, the processor is configured to perform the analysis in real time during treatment.

Optionally, the motion comprises a real or artificial motion.

Optionally, the analysis comprises a time-resolved analysis.

A product includes a non-transitory medium storing a set of instructions, an execution of which by a processor causes a method to be performed, the method comprising: obtaining a first image that corresponds with a first multi-leaf collimator (MLC) configuration, wherein the first image is generated when the MLC is stationary; obtaining a second image that corresponds with a second MLC configuration, wherein the second image is generated when the MLC and/or another component of a radiation machine is being operated to track a motion; performing an analysis based at least in part on the first image and the second image to obtain a result; and storing the result.

A method includes: obtaining a first set of images that are created while the MLC is in different respective static configurations; obtaining an input image that is created while the MLC is being operated to track a motion; selecting one or more images from the first set of images that correspond with the input image; performing an analysis based at least in part on the selected one or more images and the input image using a processor to obtain a result; and storing the result in a non-transitory medium.

Optionally, the analysis is performed to verify a treatment plan before a treatment is performed.

Optionally, the analysis is performed to verify treatment.

Optionally, the analysis is performed in real time during treatment.

Optionally, the motion comprises a real or artificial motion.

An apparatus includes: a processor configured for: obtaining a first set of images that are created while the MLC is in different respective static configurations, obtaining an input image that is created while the MLC is being operated to track a motion, selecting one or more images from the first set of images that correspond with the input image, and performing an analysis based at least in part on the selected one or more images and the input image to obtain a result; and a non-transitory medium for storing the result.

Optionally, the processor is configured to perform the analysis to verify a treatment plan before a treatment is performed.

Optionally, the processor is configured to perform the analysis to verify treatment.

Optionally, the processor is configured to perform the analysis in real time during treatment.

Optionally, the motion comprises a real or artificial motion.

A product includes a non-transitory medium storing a set of instructions, an execution of which by a processor causes a method to be performed, the method comprising: obtaining a first set of images that are created while the MLC is in different respective static configurations; obtaining an input image that is created while the MLC is being operated to track a motion; selecting one or more images from the first set of images that correspond with the input image; performing an analysis based at least in part on the selected one or more images and the input image to obtain a result; and storing the result.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
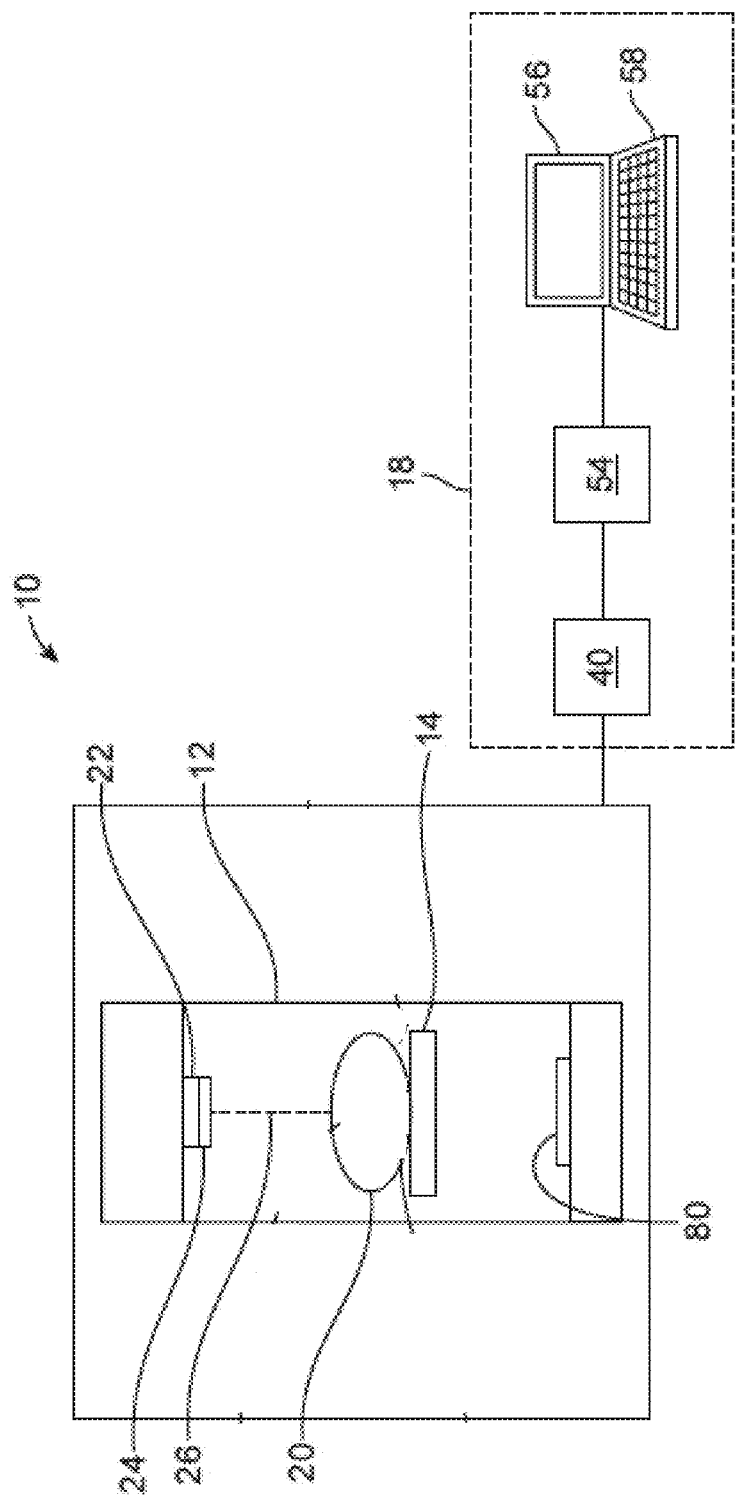
FIG. 1 illustrates a radiation treatment system.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

Figure 2:
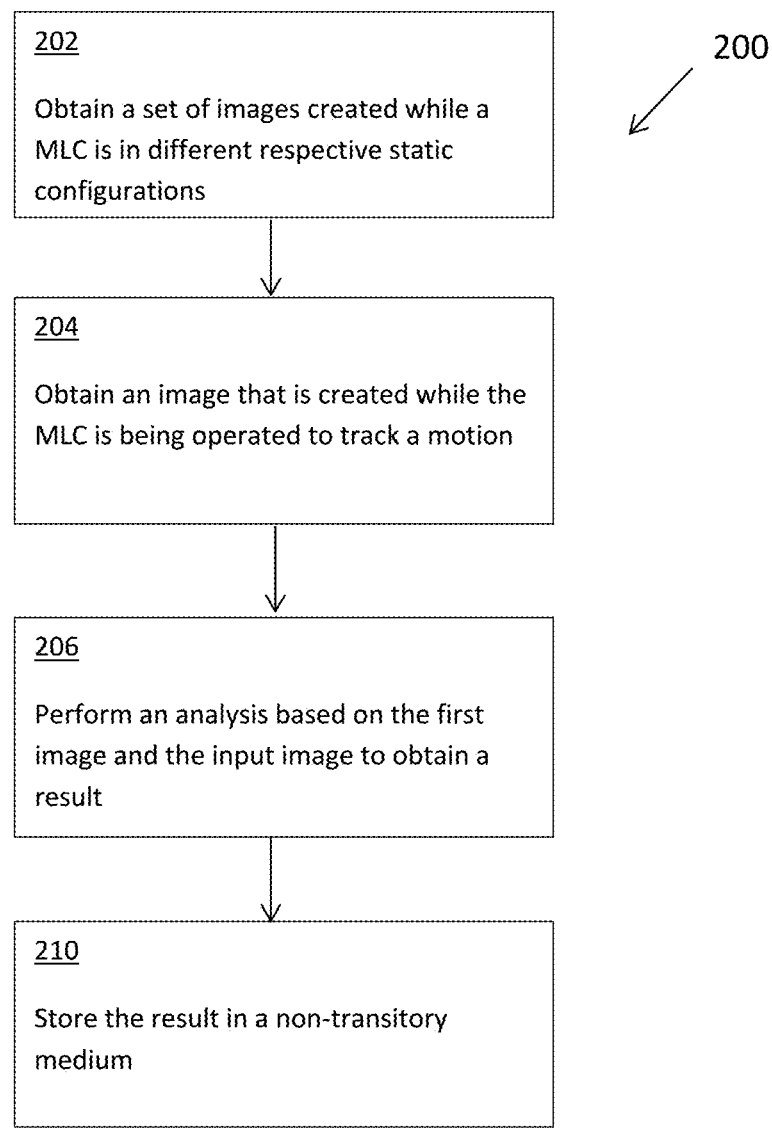
FIG. 2 illustrates a method for evaluating motion tracking.

FIG. 2 illustrates a method 200 for evaluating motion tracking. First, a set of images that are created while the MLC is in different respective static configurations is obtained (item 202). In some cases, item 202 may be accomplished by a processing unit (e.g., processing unit 54 or another processing unit) accessing the set of images. In other cases, item 202 may be accomplished by the processing unit receiving the set of images.

In further cases, the act of obtaining the set of images may include creating the set of images. Various techniques may be employed to create the set of images. In one implementation, the MLC 24 on the radiation machine 10 may be operated to achieve a desired static configuration that corresponds with a position of a target at a time point. Then the radiation machine 10 may be activated to deliver radiation. The radiation emitted from the radiation source goes through an opening created by the MLC 24 to reach the imager 80. The imager 80 then generates image signals in response to the detected radiation. In some cases, the imager 80 is an on-board imager that is configured to operate with the radiation source of the treatment radiation machine 10. For example, the imager 80 may be a MV imager that is configured to generate image signals in response to treatment radiation (e.g., radiation in the MV range). The image signals may then be stored in a non-transitory medium as an image. The above technique may be repeated for generating additional images that correspond to respective positions of the target at different respective time points. After the images are generated, the images may then be stored in the non-transitory medium as a set.

Figure 3A:
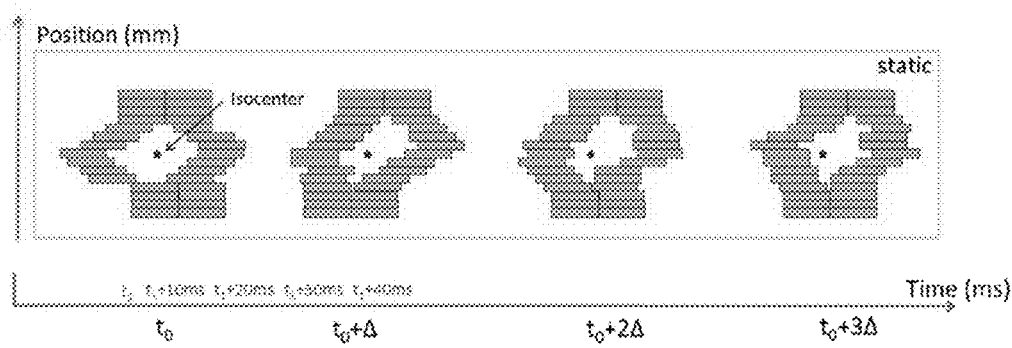
FIG. 3A illustrates examples of multi-leaf collimator (MLC) static configurations.

FIG. 3A shows examples of different MLC static configurations that may be achieved by the MLC 24 for the different respective images. The MLC static configuration at time t0 represents a desired static configuration of the leafs of the MLC 24 with respect to an isocenter at time=t0. The MLC static configuration at time t0+Δ represents a desired configuration of the leafs of the MLC 24 with respect to an isocenter at time t=t0+Δ. The same applies for the MLC static configurations at time t0+2Δ and t0+3Δ. In each of the four static cases, the isocenter is not moving with time, as indicated by the static position and the time axis below. The four instances of the MLC patterns for a dynamic MLC treatment (e.g., IMRT, VMAT, etc.) are shown indicating time-resolved image acquisition at a given frame rate with Δ being the time between two image acquisitions. Although only four static MLC configurations are shown in the set, in other examples, there may be more than four static MLC configurations or fewer than four static MLC configurations. Also, in other examples, instead of having the different static MLC configurations at different respective times that are separated by a constant time interval Δ, the different respective times may be separated by different time intervals. In some cases, there may be two image sequences for comparison. The first image sequence may have a static isocenter (but the MLC leaves may still be moving in the case of IMRT/VMAT). The second image sequence may be with moving isocenter. Both image sequences may be obtained using a high frame rate, e.g., 10-25 Hz, and may be synchronized later during analysis in order to compare the images from both sequences. Also, in some cases, the images may be acquired with an acquisition rate (or frequency) that is less than the heartbeat of the machine (which may be 10 ms or 100 Hz).

Returning to FIG. 2, next, an input image that is created while the MLC is being operated to track a motion is obtained (item 204). In some cases, item 204 may be accomplished by a processing unit (e.g., processing unit 54 or another processing unit) accessing the input image. In other cases, item 204 may be accomplished by the processing unit receiving the input image.

In further cases, the act of obtaining the input image may include creating the input image. In one implementation, motion data representing a motion may be inputted into the processing unit, and the processing unit may then operate the MLC 24 and/or other component(s) of a radiation machine 10 based on the motion data to track the motion. The motion may be a real motion of at least a part of a person, or alternatively, an artificial motion (e.g., a model representing a simulated motion). At a certain time point that corresponds with one of the images in the set of images (obtained in item 202), the radiation machine 10 may be activated to deliver radiation. The radiation emitted from the radiation source 22 and go through an opening created by the MLC 24 to reach the imager 80. The imager 80 then generates image signals in response to the detected radiation. In some cases, the imager 80 is an on-board imager that is configured to operate with the radiation source of the treatment radiation machine. For example, the imager 80 may be a MV imager that is configured to generate image signals in response to treatment radiation (e.g., radiation in the MV range). The image signals may then be stored in a non-transitory medium as an input image. Because the input image is generated while the MLC 24 and/or other component(s) of the radiation machine 10 is operated to track the motion, the input image includes information indicating how well the motion is tracked. The above technique may be repeated for generating additional input images that correspond to respective tracked positions of the target at different respective time points. In some cases, as the input images are generated, they may be stored in the non-transitory medium.

In the above embodiments, the input image is generated at a certain time point that corresponds with one of the images (reference images) in the set of images (obtained in item 202). In other embodiments, the input image may be generated based on other criteria, and the time at which the input image is generated may or may not correspond with any of the reference images in the set of images obtained in item 202. For example, the input image may be generated at a time that is between two time points of two respective reference images in the set of images obtained in item 202. In such cases, the processing unit may process the two reference images to determine an "intermediate" image that corresponds with the time point of the input image. In one implementation, if a leaf of the MLC 24 is configured to move from position X1 at time point t1 to position X2 at time point t2, and if the input image is generated at time point t' that is between t1 and t2, then the intermediate leaf position X' of the intermediate image may be calculated by the processing unit as $X'=(X2-X1)*t'/(t2-t1)$. The same calculation may be performed by the processing unit for all of the remaining leafs so that an intermediate MLC pattern may be created for the intermediate image for comparison with the input image. In other cases, instead of calculating intermediate image(s), the processing unit may select the closest neighbor image in one image sequence for analysis (e.g., comparison) with the image from the other image sequence.

Figure 3B:
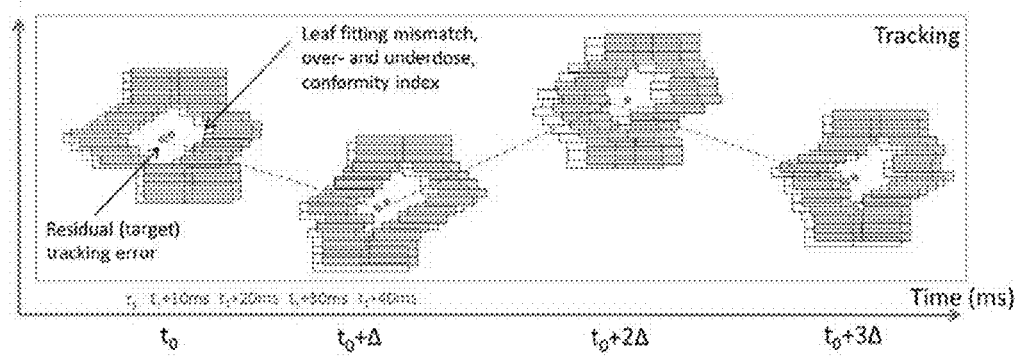
FIG. 3B illustrates examples of MLC configurations during tracking of a motion.

FIG. 3B shows examples of different MLC configurations that may be achieved by the MLC 24 at different time points while tracking a motion. During treatment, a target may move. In each diagram, the white MLC configuration represents a shifted position of a planned MLC configuration, which is shifted according to known target shift without any tracking error. In particular, as shown in the figure, the white MLC configuration at time=t0 is the same MLC static configuration shown in FIG. 3A at time=t0, but shifted in position according to known movement. The known movement may be obtained from positional data representing motion of a patient, or positional data representing an artificial position. In some cases, the known movement may be obtained from positional data in a treatment plan. As shown in FIG. 3B, the shaded MLC configuration represents the actual MLC configuration achieved at the respective time point. It should be noted that the logged isocenter position (associated with the shaded MLC configuration) is not identical with the shifted one from the static case, as the tracking system needs to compensate the system latency and applies a prediction model, which has some inherent prediction error. In particular, during an operation, the tracking system that is configured to track a motion of the patient may apply a prediction model to compensate for latency of the radiation system (e.g., latency due to processing time and/or lag in components' operations). The prediction model has an inherent prediction error. This inherent prediction error, in turn, results in residual (target) tracking error. If it is assumed that the planned, given MLC pattern, is shifted according to the known target shift without any tracking error, the white MLC pattern shown in FIG. 3B is achieved. However, due to prediction error (e.g., error in the prediction of position) and/or due to MLC system characteristics (e.g., acceleration, inertness, travel range, delay in mechanical motion, delay in processing time, etc.), the actual MLC shape (represented by the shaded MLC leafs) is different from the white MLC configuration. Such difference will result in overdose area(s) and/or underdose area(s), leading to dosimetric changes compared to the static case. Also, the isocenter position logged from the operation of the system is linked to the latency of the system. The logged isocenter position provides the real isocenter position that may be used at a later point in time for analysis. For example, the logged isocenter position may be used to determine errors of the prediction model.

In the above embodiments, the reference images and the input images are described as being generated using the same MLC 24 at the same radiation system 10. In other embodiments, the reference images may be generated using a first MLC at a first radiation system, and the input images may be generated using a second MLC at a second radiation system. The first MLC may be identical or similar to the second MLC. For example, the first radiation system with the first MLC may be a simulation system configured to perform treatment simulation and/or treatment planning. The second radiation system with the second MLC may be a treatment system. Also, in some embodiments, the reference images and the input images may be generated using different respective energies, or the same energy.

Returning to FIG. 2, next, an analysis is performed based on the one of the reference images (e.g., first image) and the input image to obtain a result (item 206). In some cases, the analysis may be a time-resolved analysis performed by the processing unit (e.g., the processing unit 54 or another processing unit). For example, the processing unit may synchronize the input image with one or more reference images to a common time base. Various techniques may be employed to achieve this objective. In one embodiment, the processing unit may select one of the reference images that correspond (e.g., in time along a known motion pattern) with the input image. In another embodiment, if the input image falls between two time points for two of the reference images along the known motion pattern, then the processing unit may select two reference images from the first set of reference images, and may perform an interpolation based on the two reference images to determine an interpolated parameter that corresponds with the input image. In a further embodiment, the input image from tracking may be generated at a time that corresponds with one of the reference image. In such cases, the "selecting" of the reference image for processing with the input image may be considered as being performed before the input image is generated. In such cases, the processing unit may not need to perform synchronization between the input image and the reference image after the input image is generated.

Also, in item 206, the processing unit may be configured to compare the reference image with the input image acquired during the tracking session to determine one or more time-resolved parameter(s), such as overdose and/or underdose areas (conformity index), dose difference, gamma, maximum dose of CTV and/or PTV projected to an image plane, minimum dose of CTV and/or PTV projected to an image plane, average dose of CTV and/or PTV projected to an image plane, etc. Some of these parameters are further described below.

Overdose and underdose areas: Overdose area is the area which is related to overexposure based on the actual MLC shape versus the planned one. Underdose area is the underdosed or covered area of the MLC in the actual image. These parameters may be determined by the processing unit from the MLC shape analysis of the acquired images.

Dose difference: In some cases, the MV imager is first calibrated in absolute dose in units of Gy. The dose difference may then be determined by the processing unit by analyzing the two images.

Gamma refers to the dose difference and distance to agreement. Gamma values provide a quantitative evaluation of dose distributions. Here two images are being compared not only in terms of dose difference but also in terms of distance to agreement.

Dose analyzes in clinical target volume (CTV), planning target volume (PTV) and any other target volumes previously outlined during treatment planning may be performed by the processing unit. For example, the processing unit may perform 3D-to-2D projection of the volumes to the acquired image plane, and may then analyze the absolute dose values in the defined image part. In case the 3D dose distribution is calculated in a time resolved manner within the patient (time resolved 3D or in-vivo dosimetry), the processing unit may perform the analysis in the respective 3D volume of the patient.

The processing unit may perform other types of analysis in other examples.

In some cases, the analysis may involve comparing the reference image obtained when the MLC 24 is in a static configuration, with the input image that is obtained during motion tracking. Also, in some cases, the analysis (e.g., comparing of the reference image with the input image) may be performed in real time. For example, the processing unit may perform the analysis shortly (e.g., within 1 second, and more preferably within 0.5 second) after the input image is obtained. In other cases, the analysis may be performed by the processing unit retrospectively. For example, in other embodiments, a set of reference images and a set of input images are obtained. Each reference image corresponds with a desired static MLC configuration shifted by a certain position that corresponds with a certain time point, and each input image corresponds with an actual MLC configuration achieved during motion tracking. After the set of reference images and the set of input images are obtained, the two sets of images are then synchronized to a common time axis. The processing unit may then perform the analysis based on the synchronization.

As discussed, the input image may be synchronized with one of the reference images that are generated when the MLC 24 is in a static configuration. Accordingly, the processing unit may be configured to perform the analysis based at least in part on the reference image and the input image to obtain a result. Also, as discussed, in one scenario, one reference image corresponding with the input image may be selected from the set of reference images. In another scenario, if the input image is temporally between the time points of two reference images, then the two reference images may be selected from the set of reference images, and the processing unit may perform an interpolation to obtain an interpolation value based on the two reference images that correspond with the input image. In such cases, either or both of the two reference images may be considered as corresponding with the input image since they are the closest in time to the input image. In either of the above two scenarios, the processing unit may be considered as performing the analysis based at least in part on the reference image (one selected reference image in the first scenario, and either one of the reference images in the second scenario) and the input image.

Also, in some cases, the imager 80 is configured to measure time-resolved photon (energy) fluence or absorbed dose based on the time-resolved measured signal of the actual beam. It should be noted that a MV imager, without proper calibration, measures a signal related to photon fluence, and does not measure dose. Thus, in order to use a MV imager to determine dose, a calibration procedure is used to calibrate the images so that dose information may be determined.

After the result is obtained, the result may then be stored in a non-transitory medium (item 210). In some cases, the method 200 may optionally further include displaying the result in a screen for viewing by a user.

In some cases, the method 200 may be performed before treatment is delivered to a patient. For example, the method 200 may be performed to determine machine quality assurance. As another example, the method 200 may also be performed to verify a treatment plan, and/or to determine pre-treatment quality assurance. In some embodiments, if the method 200 is performed before treatment is delivered to a patient (e.g., for machine quality assurance, pre-treatment quality assurance, etc.), the method 200 may be performed without using any phantom and without use of any motion platform.

In one implementation, to perform machine QA for MLC tracking, an executable tracking plan is first loaded on the treatment delivery system (the radiation machine for which the machine QA is being performed), and the treatment delivery system is set to operate in QA mode. Also, a target motion trajectory is input into a tracking engine at the treatment delivery system. The target motion trajectory being used here may be an artificial trajectory or a generic clinical trajectory. The tracking engine at the treatment delivery system is configured to operate various components (e.g., MLC, patient support, gantry, etc.) of the treatment machine to follow the motion trajectory of a target. Since no real target is being used here, and no real motion of any real target is being used, the tracking engine will utilize the inputted target motion trajectory as the motion to follow.

Also, before the QA session, dosimetric calibration of the imager 80 (e.g., EPID) for pre-treatment verification may be performed. In some cases, for MV image calibration, various MV images at different imager positions are being acquired using various field sizes, energies and dose rates. These images are then used to determine a pixel sensitivity map, and certain parameter(s) that will allow the grey values of the image(s) to be converted into absorbed dose values in a given depth in water (e.g. 5 cm). From this process, a specific model is applied and some parameters of this model are adapted based on the calibration process.

After the treatment machine is set up for QA, the user then operates the treatment machine to execute the QA plan. The QA plan includes two parts. The first part of the QA plan causes the treatment machine to generate a set of reference images corresponding with different respective static configurations of the MLC 24 (static case). For example, the first part of the QA plan may prescribe that a first static image be generated when the MLC 24 is in a first configuration that corresponds with a time point t1 along the motion trajectory, and that a second static image be generated when the MLC 24 is in a second configuration that corresponds with another time point t2 along the motion trajectory. The second part of the QA plan causes the treatment machine to generate a set of input images while the treatment machine performs tracking, e.g., performs MLC compensation based on the input target motion trajectory (dynamic case). In some cases, the first part of the QA plan may be achieved using a static MLC plan. In other cases, the first part of the QA plan may be achieved using a dynamic MLC plan. The processing unit of the QA system obtains the two sets of images, and applies dosimetric calibration to each frame in both set of images—the images generated when MLC 24 is in static configuration (static images), and images generated during tracking (motion images) according to a tracking plan being evaluated. The processing unit also synchronizes both set of images to a common time axis to enable comparison between static and motion compensated delivery. It should be noted that the logged target position obtained from the tracking may not be identical to the known target position (based on known target trajectory used in generating the static images) due to latency and prediction errors associated with the tracking plan being evaluated. In some embodiments, the processing unit may be configured to, based on the logged target position, compare each motion image (e.g., an EPID frame) shifted by the known isocenter shift at the corresponding point in time, with a corresponding static image. The amount of shift is known from the isocenter position during treatment, which is after the fact known without the help of any prediction algorithm. In some cases, the processing unit may also determine one or more parameters integrated over time based on the time resolved analysis. In some embodiments, the processing unit determines quantitative parameter(s), such as gamma, dose difference, shift, conformity index, and maximum dose, mean dose, and minimum dose in the projected PTV and/or CTV being analyzed. The processing unit then generates a detailed report summarizing the result of the analysis, to enable a user to either accept or decline a tracking plan.

In one implementation, to perform pre-treatment QA (e.g., to evaluate a treatment plan) for MLC tracking, an executable tracking plan (prescribed by the treatment plan being evaluated) is first loaded on the treatment delivery system. Also, a target motion trajectory is input into a tracking engine at the treatment delivery system. Unlike machine QA, the target motion trajectory being used here may be one that is for a specific patient which plan needs to be verified. In some cases, the motion trajectory may be a previously acquired target motion based on a planning (e.g., simulation) 4D-CT or a fluoroscopic image stream, or any other method leading to this information. Also, in some embodiments, if the user wants to simulate target motion deviations, variations of the previously acquired target motion, or a generic family of target motion patterns, may be input into the treatment machine for the pre-treatment verification. After the treatment machine is set up for pre-treatment QA, the user then operates the treatment machine to execute the QA plan. The rest of the process is the same or similar to that described for machine QA, and therefore will not be repeated here.

In some embodiments, for machine QA and pre-treatment QA, no phantom or motion platform is required with the above technique. This is because the input for motion compensation may be a previously generated motion pattern in case of machine QA, or an already captured target motion input signal of a patient obtained for treatment planning.

In other cases, the method 200 may be performed during a treatment session. For example, the method 200 may be performed to determine quality assurance of the treatment during a treatment session. In one implementation, the method 200 may be performed in real time during treatment. In such cases, the performing of the analysis (item 206) may be performed by the processing unit in real time (i.e., at a time that is shortly (e.g., less than 1 second, and more preferably less than 0.5 second, and even more preferably less than 0.2 second) after an input image is generated by the imager) during treatment. In other cases, the performing of the analysis (item 206) may be performed by the processing unit between two deliveries of radiation beam during a treatment session. In such cases, the performing of the analysis may or may not be accomplished in real time.

In one implementation for during-treatment QA, the same concept as that for pre-treatment QA is used, except that the target motion trajectory is not known a priori. Thus, the motion trajectory is the actual motion of the patient that is measured during the treatment. During treatment, the tracking engine of the treatment machine performs motion compensation based on a tracking plan—e.g., operates various components (including the MLC 24) to track the motion of the actual target. Also while this is happening, the imager 80 generates EPID images that correspond with different respective configurations of the MLC 24 while the MLC 24 is tracking the target. During the treatment, various real time data (e.g., substantially real time, such as time that is within 1 second and more preferably within 0.5 second of the current time) may be available. For example, calibrated time resolved EPID images for transit dosimetry based on 4D CT/CBCT patient data, the actual target motion trajectory, MLC shapes, etc., are available for use by the processing unit to perform its analysis. In some embodiments, the processing unit is configured to compare these real time data acquired during treatment, with previously calculated transit dosimetry 2D dose distributions based on a static CT/CBCT data set, and also dynamic MLC shape (in the case of IMRT or VMAT). If there is any major deficiency (e.g., deficiency exceeding a certain threshold) of the tracking system that are detected by the processing unit during treatment, the processing unit may then switch off the therapeutic radiation beam. For example, if a parameter derived from the static 2D dose distribution differs significantly (e.g., exceeding a certain threshold) from that derived from the during-treatment 2D dose distribution, the processing unit may generate a control signal to stop the delivery of the treatment beam.

In further cases, the method 200 may be performed after a treatment session to evaluate the performance of the treatment. For example, the processing unit of the QA system may retrospectively calculate the time resolved transit portal dose images based on the available patient data of the day, the logged target position, and the given (e.g., shifted static) MLC shape, to quantify dosimetric errors based on the actual MLC shape applied.

Also, in some embodiments, the method 200 may include determining time resolved in-vivo dosimetry for MLC tracking. For example, the processing unit of the QA system may be configured to reconstruct the 3D dose distribution within the patient based on acquired time resolved pre-treatment data, and to compare this with the planned 3D dose distribution retrospectively. In some cases, the processing unit may use available data after the treatment, such as actual target motion trajectory, 4D CT/CBCT, time resolved transit dose images, etc. Also, in some embodiments, the processing unit may map time resolved 3D dose distributions to a common CT reference in order to compare them with planned 3D dose distribution.

In one or more embodiments described herein, the imager 80, the MLC 24, and the processing unit (that is configured to perform the analysis for QA) may be considered to be parts of a QA system configured to perform QA based on MLC tracking. In some cases, the imager 80 may be an EPID calibrated to measure time-resolved photon fluence, or absorbed dose, based on the time resolved measured signal of the actual beam. The EPID-based QA system described herein will work for all beam energies and dose rates, including those associated with flattening filter free beams. In some embodiments, a pixel sensitivity correction map may be applied for the EPID, which may depend on the beam energy and/or dose rate that are involved. The QA system may be configured to shift images (e.g., EPID images) from the imager 80 obtained during a tracking session based on known target trajectory, as similarly discussed. In some cases, the shifting of the images may be combined with time resolved absolute portal dosimetry to provide QA (e.g., machine QA, pre-treatment QA, etc.) for evaluating MLC tracking plans. Also, in some cases, the QA method may be performed without using any phantom and based on measurements derived from images provided by the imager 80.

In one implementation, the processing unit of the QA system may include different modules for performing different functions described herein. For example, the processing unit may include a first input module configured to obtain the set of images that are created while the MLC 24 is in different respective static configurations. Such first input module may be configured to access a medium (e.g., storage, database, etc.) to obtain the images. Also, the processing unit may include a second input module configured to obtain an image that is created while the MLC 24 is being operated to track a motion. Furthermore, the processing unit may include an imager shifter configured to shift the image from the imager 80 obtained during a tracking session based on known target trajectory. In some cases, EPID or MV images acquired during the tracking session may be shifted based on the known isocenter position on the imager (this information may be obtained based on the known real isocenter position at the same time instance as the images have been acquired), and the current isocenter (which is known and not changing throughout the session, as the imager will not be moved based on the isocenter shift acquired). In one implementation, the processing unit may be configured to shift and re-bin the MV images of the tracking run to a common grid, which then will allow the images to be compared with those from the non-tracking run after the time axes have been synchronized.

In addition, the processing unit may include time-resolved parameter(s) determination module configured to determine one or more time-resolved parameter(s), such as overdose and/or underdose areas (conformity index), dose difference, gamma, maximum dose of CTV and/or PTV projected to an image plane, minimum dose of CTV and/or PTV projected to an image plane, average dose of CTV and/or PTV projected to an image plane, etc.

Optionally, the QA system may also be configured to reconstruct three dimensional (3D) dose in a virtual phantom to compare 3D dose distributions for various target motion compensation strategies. For example, there may be one strategy for compensating target motion that involves shifting a patient support. There may also be another strategy for compensating target motion that involves rotating the MLC 24. The QA system described herein may include a motion compensation comparison module configured to compare different strategies for compensating target motion. The motion compensation comparison module may calculate 3D dose distributions based on image data obtained from the imager 80 for different strategies, and may transmit the comparison to a screen for presentation to a user. Other motion compensation strategies, such as integrated-target-volume (ITV) based approaches, may also be used. ITV is an integration of the CTV over time in case of moving CTVs. In some cases, the comparison may involve evaluating dosimetric impact based on tracking parameter(s) involved in the tracking strategies, such as tracking limits, dose rates, motion trajectories, etc.

In one or more embodiments described herein, the imager 80 described with reference to the method 200 may be an electronic portal imaging device (EPID) that is fully integrated and automated for providing image data for pre-treatment QA, during-treatment QA, and/or post-treatment QA. The imager 80 operates with the MLC 24 that performs beam tracking for target motion compensation. The system and method described herein may be used with dynamic beam delivery techniques, such as IMRT and VMAT, which may require extensive QA prior to clinical application to patients. In some cases, the beam delivery system may be extensively checked and each patient's treatment plan may be delivered to a QA phantom or EPID, and analyzed prior to application to the patient to verify that the treatment plan can be delivered safely and is dosimetrically accurate. Beam tracking adds an additional layer of complexity and risk for the patient, as the actual beam delivery cannot be predicted because it depends on the actual target motion during beam delivery, which is not known prior to treatment. In addition, a beam tracking system may face technical challenges as there are unavoidable system latencies that need to be compensated by motion prediction tools and mechanical components (e.g., MLC) subject to system limitations, such as speed of motion and range of travel. One or more embodiments of the system and method described herein provide machine QA, pre-treatment QA, and during-treatment QA, for beam tracking, in order to ensure accurate and safe beam delivery prior to, and at any time during, treatment. One or more embodiments of the system and method described herein also provide time-resolved real time transit dosimetry and time-resolved real time in-vivo dosimetry while considering beam tracking. Transit dosimetry may be achieved by comparing 2D dose images. In some cases, the transmitted photon fluence measured with the help of the MV imager may provide measured gray values, from which dose values may be derived. The dose values may be in a form of a 2D image. This is then compared with the calculated 2D dose transmitted through the patient. In-vivo dosimetry involves a procedure for determining the dose within a patient (in-vivo). The in-vivo dosimetry may be a 3D dose distribution based on the measured transmitted dose, which may be reconstructed in a most recent 3D patient representation, such as the 3D or 4D CBCT acquired just prior treatment.

In the case of transit and in-vivo QA, the actual target motion of the patient under treatment may be used to for the beam tracking. Also, in some embodiments, for transit dosimetry and in-vivo dosimetry, the processing module may determine the applied dose to the patient, and may use such information to adjust (e.g., fine tune) a treatment plan for a particular patient for subsequent treatment fractions. Furthermore, in one or more embodiments described herein, the processing unit may include a 3D dose distribution determination module configured to calculate actual 3D dose distribution applied during a tracking session, and compare such 3D dose distribution to a prescribed 3D dose distribution.

Computer System Architecture

Figure 4:
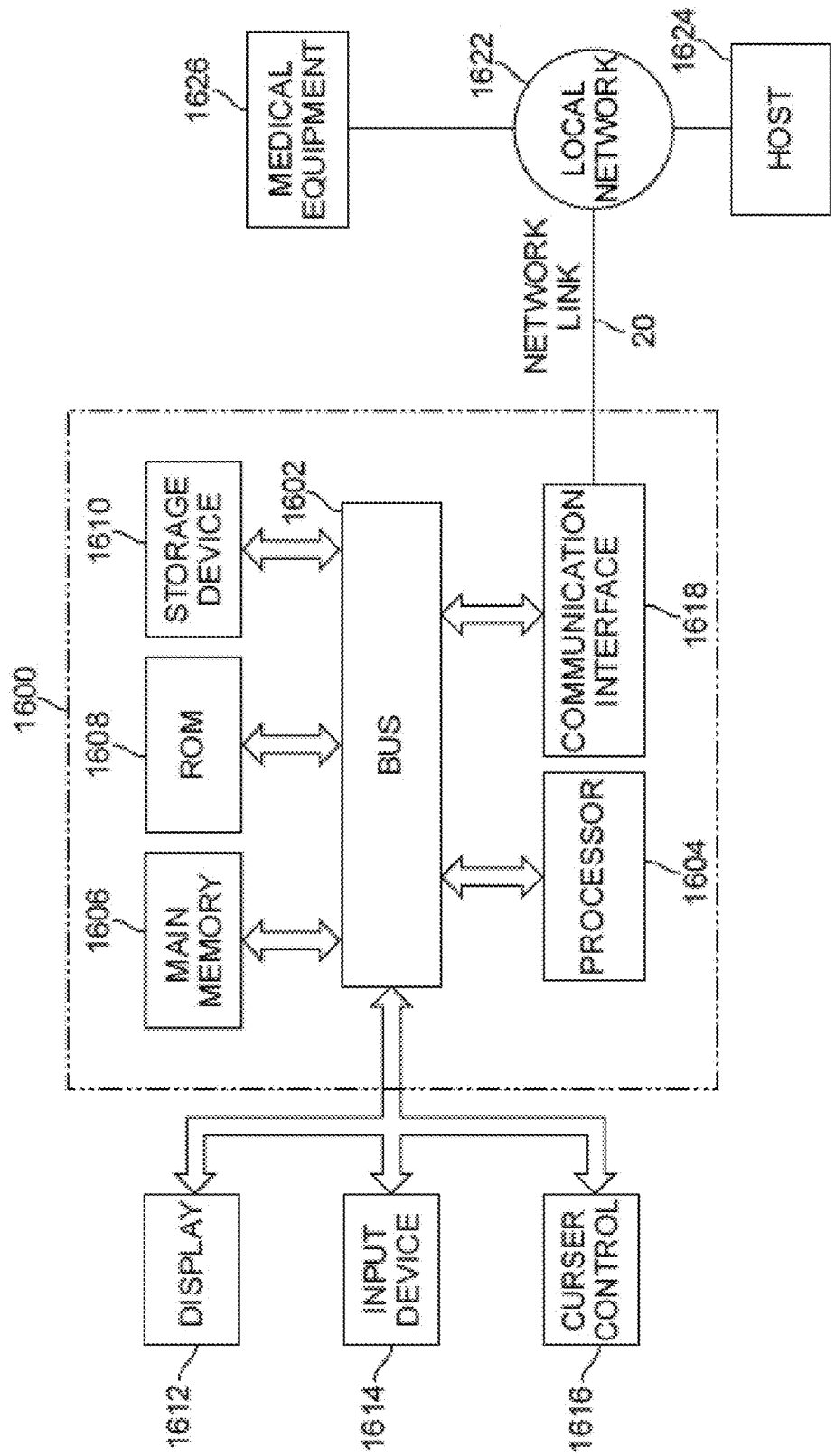
FIG. 4 illustrates a computer system with which embodiments described herein may be implemented.

FIG. 4 is a block diagram illustrating an embodiment of a computer system 1600 that can be used to implement various embodiments described herein. For example, the computer system 1600 may be configured to implement the method of FIG. 2 in accordance with some embodiments. Also, in some embodiments, the computer system 1600 may be used to implement the processing unit 54 of FIG. 1, or any processing unit described herein.

Computer system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network(s), the network link 1620, and the communication interface 1618.

It should be noted that as used in this specification, the term "image" does not necessarily refer to an image that is visually displayed, and may refer to image (e.g., image data) that is stored or processed without visually displayed. Also, terms like "first", "second", "third", etc., do not necessarily convey order, and may be used to refer to different items. For example, "first image" and "second image" do not necessarily refer to an image that is the first in order and an image that is in the second in order, unless specifically stated otherwise. Rather, "first image" and "second image" may be used to refer to two individual images.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:
1. A method comprising:
obtaining a first image that corresponds with a first multi-leaf collimator (MLC) configuration, wherein the first image is generated when the MLC is stationary;
obtaining a second image that corresponds with a second MLC configuration, wherein the second image is generated when the MLC and/or another component of a radiation machine is being operated to track a motion;
performing an analysis based at least in part on the first image and the second image using a processor to obtain a result; and
storing the result in a non-transitory medium;
wherein the method further comprises performing an interpolation based on the first image and a third image to determine an interpolated parameter that corresponds with the second image; and wherein the analysis is performed to verify a treatment plan or to verify treatment.

2. The method of claim 1, wherein the first image is a part of a first set of images that are obtained while the MLC is in different respective static configurations.

3. The method of claim 2, further comprising selecting the first image from the first set of images that corresponds with the second image.

4. The method of claim 1, wherein the analysis is performed in real time during treatment.

5. The method of claim 1, wherein the motion comprises a real or artificial motion.

6. The method of claim 1, wherein the analysis comprises a time-resolved analysis.

7. An apparatus comprising:
a processor configured for
obtaining a first image that corresponds with a first multi-leaf collimator (MLC) configuration, wherein the first image is generated when the MLC is stationary,
obtaining a second image that corresponds with a second MLC configuration, wherein the second image is generated when the MLC and/or another component of a radiation machine is being operated to track a motion, and
performing an analysis based at least in part on the first image and the second image to obtain a result; and
a non-transitory medium for storing the result;
wherein the processor is further configured for performing an interpolation based on the first image and a third image to determine an interpolated parameter that corresponds with the second image; and
wherein the processor is configured to perform the analysis to verify a treatment plan or to verify treatment.

8. The apparatus of claim 7, wherein the first image is a part of a first set of images that are obtained while the MLC is in different respective static configurations.

9. The apparatus of claim 8, wherein the processor is further configured for selecting the first image from the first set of images that corresponds with the second image.

10. The apparatus of claim 7, wherein the processor is configured to perform the analysis in real time during treatment.

11. The apparatus of claim 7, wherein the motion comprises a real or artificial motion.

12. The apparatus of claim 7, wherein the analysis comprises a time-resolved analysis.

13. A product having a non-transitory medium storing a set of instructions, an execution of which by a processor causes a method to be performed, the method comprising:
obtaining a first image that corresponds with a first multi-leaf collimator (MLC) configuration, wherein the first image is generated when the MLC is stationary;
obtaining a second image that corresponds with a second MLC configuration, wherein the second image is generated when the MLC and/or another component of a radiation machine is being operated to track a motion;
performing an analysis based at least in part on the first image and the second image to obtain a result; and
storing the result;
wherein the method further comprises performing an interpolation based on the first image and a third image to determine an interpolated parameter that corresponds with the second image; and
wherein the analysis is performed for verifying a treatment plan or for verifying treatment.

14. A method comprising:
obtaining a first set of images that are created while a first multi-leaf collimator (MLC) is in different respective static configurations;
obtaining an input image that is created while the MLC is being operated to track a motion;
selecting a plurality of images from the first set of images;
performing an interpolation based on the selected plurality of images to determine an interpolated parameter that corresponds with the input image;
performing an analysis based at least in part on the selected plurality of images and the input image using a processor to obtain a result; and
storing the result in a non-transitory medium;
wherein the analysis is performed to verify a treatment plan or to verify treatment.

15. The method of claim 14, wherein the analysis is performed in real time during treatment.

16. The method of claim 14, wherein the motion comprises a real or artificial motion.

17. An apparatus comprising:
a processor configured for:
obtaining a first set of images that are created while a first multi-leaf collimator (MLC) is in different respective static configurations,
obtaining an input image that is created while the MLC is being operated to track a motion,
selecting a plurality of images from the first set of images,
performing an interpolation based on the selected plurality of images to determine an interpolated parameter that corresponds with the input image,
performing an analysis based at least in part on the selected plurality of images and the input image to verify a treatment plan or to verify treatment; and
a non-transitory medium for storing the result.

18. The apparatus of claim 17, wherein the processor is configured to perform the analysis in real time during treatment.

19. The apparatus of claim 17, wherein the motion comprises a real or artificial motion.

20. A product having a non-transitory medium storing a set of instructions, an execution of which by a processor causes a method to be performed, the method comprising:
obtaining a first set of images that are created while a first multi-leaf collimator (MLC) is in different respective static configurations;
obtaining an input image that is created while the MLC is being operated to track a motion;
selecting a plurality of images from the first set of images;
performing an interpolation based on the selected plurality of images to determine an interpolated parameter that corresponds with the second image;
performing an analysis based at least in part on the selected plurality of images and the input image to obtain a result; and
storing the result;
wherein the analysis is performed to verify a treatment plan or to verify treatment.

* * * * *